(12) United States Patent
Gruzdev et al.

(10) Patent No.: US 7,548,568 B2
(45) Date of Patent: Jun. 16, 2009

(54) PORTABLE LASER DEVICE

(75) Inventors: Valentin A. Gruzdev, Moscow (RU); Pavel V. Efremkin, Ardsley, NY (US)

(73) Assignee: Innotech USA Inc., Tarrytown, NY (US)

( * ) Notice: Subject to any disclaimer, the term of this patent is extended or adjusted under 35 U.S.C. 154(b) by 45 days.

(21) Appl. No.: 11/975,572

(22) Filed: Oct. 19, 2007

(65) Prior Publication Data

US 2008/0043790 A1 Feb. 21, 2008

Related U.S. Application Data

(62) Division of application No. 10/970,870, filed on Oct. 22, 2004, now Pat. No. 7,298,767, which is a division of application No. 10/202,325, filed on Jul. 24, 2002, now Pat. No. 6,813,289.

(60) Provisional application No. 60/307,628, filed on Jul. 25, 2001.

(51) Int. Cl.
*H01S 3/04* (2006.01)
(52) U.S. Cl. .............................. 372/35; 372/34; 372/36; 165/87
(58) Field of Classification Search .................. 372/34, 372/35, 36; 165/87
See application file for complete search history.

(56) References Cited

U.S. PATENT DOCUMENTS

| 3,711,785 A | * | 1/1973 | Zitkus | 372/67 |
|---|---|---|---|---|
| 4,856,580 A | * | 8/1989 | Ley | 165/87 |
| 5,327,442 A | | 7/1994 | Yarborough et al. | |
| 5,348,552 A | | 9/1994 | Nakajima et al. | |
| 5,422,899 A | | 6/1995 | Freiberg et al. | |
| 5,432,811 A | | 7/1995 | Polushkin et al. | |
| 5,481,556 A | | 1/1996 | Daikuzono | |
| 5,548,604 A | | 8/1996 | Toepel | |
| 5,696,783 A | * | 12/1997 | Montgomery | 372/35 |
| 5,868,731 A | | 2/1999 | Budnik et al. | |
| 5,940,420 A | | 8/1999 | Blair et al. | |
| 6,122,300 A | | 9/2000 | Freiberg et al. | |
| 6,195,372 B1 | | 2/2001 | Brown | |
| 6,251,102 B1 | | 6/2001 | Gruzdev et al. | |
| 6,421,364 B2 | | 7/2002 | Lubrano | |
| 6,550,934 B2 | | 4/2003 | Tao et al. | |
| 6,589,233 B1 | | 7/2003 | Maki | |

FOREIGN PATENT DOCUMENTS

| JP | 60136385 | * | 7/1985 |
|---|---|---|---|
| JP | 63204679 | * | 8/1988 |

* cited by examiner

*Primary Examiner*—Minsun Harvey
*Assistant Examiner*—Tod T Van Roy
(74) *Attorney, Agent, or Firm*—Lawrence F. Fridman

(57) ABSTRACT

A hand-held laser device includes a casing formed with a substantially hollow interior space and having a laser emitter thereinside. The laser emitter is formed with an exciting lamp and a laser rod. A source generating a stream of gaseous coolant is provided within the interior space. A fluid cooling arrangement at least partially surrounding the laser rod is disposed within the stream of gaseous coolant for heat removal therefrom.

10 Claims, 6 Drawing Sheets

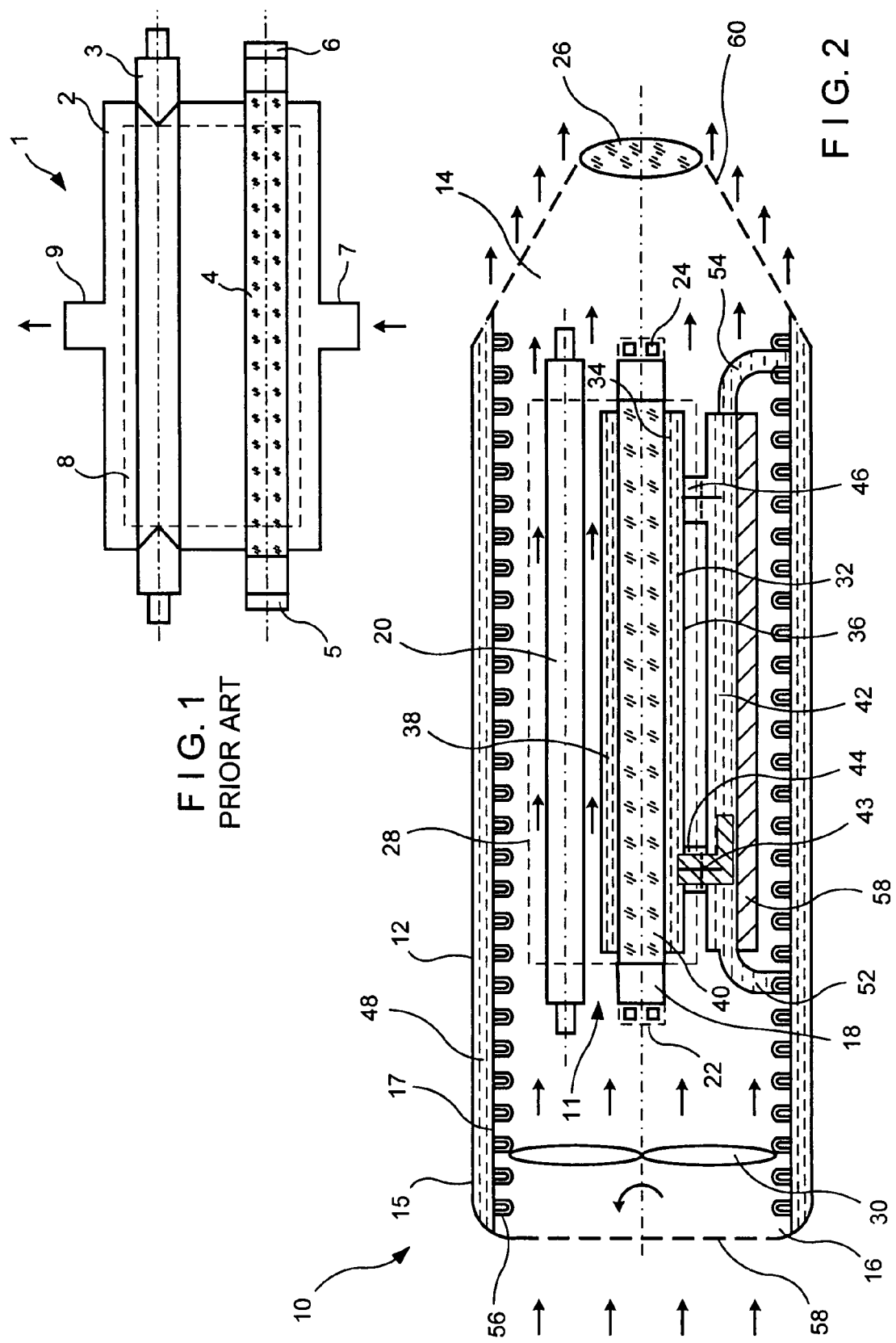

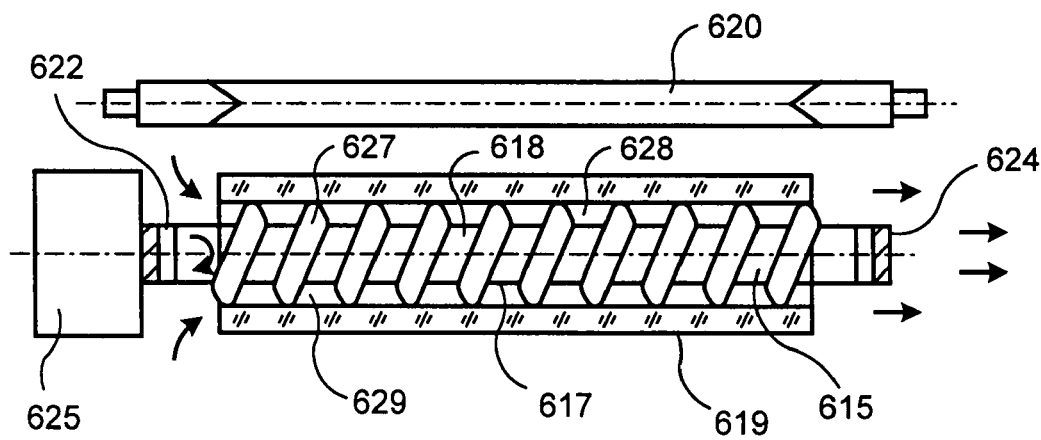
F I G. 6
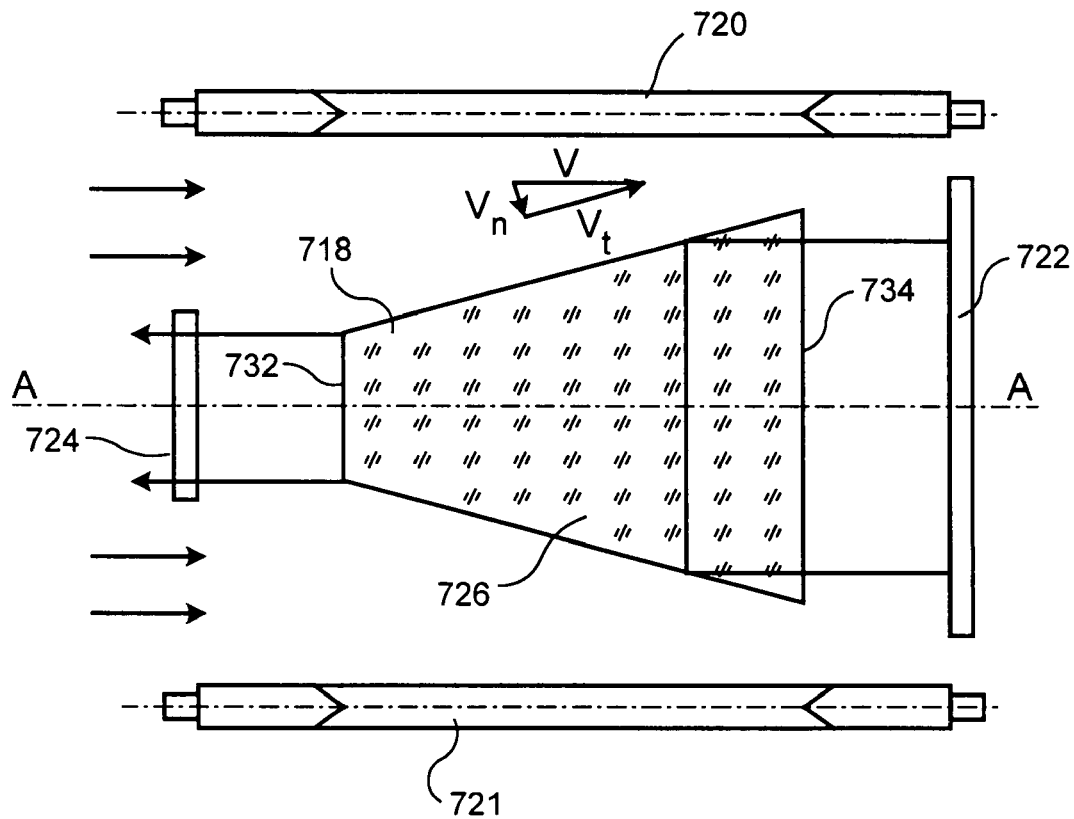
F I G. 7

PORTABLE LASER DEVICE

THIS APPLICATION IS A DIVISIONAL APPLICATION OF patent application Ser. No. 10/970,870 FILED Oct. 22, 2004, now U.S. Pat. No. 7,298,767 WHICH IS A DIVISIONAL APPLICATION OF patent application Ser. No. 10/202,325 FILED Jul. 24, 2002, (CURRENTLY U.S. Pat. No. 6,813,289.B2) CLAIMING BENEFIT UNDER 35 USC 119(e) OF THE PROVISIONAL PATENT APPLICATION 60/307,628 FILED Jul. 25, 2001.

BACKGROUND OF THE INVENTION

1. Field of the Invention

The invention relates in general to portable laser devices based on a solid-state laser technology, and in particular it relates to hand-held laser devices with direct cooling of a laser rod assembly.

2. Discussion of Background and Prior Art

The laser radiation generated by solid-state lasers is widely used in the industry and medicine. As illustrated in FIG. 1 a typical laser emitted assembly consists of a laser rod 6, an exciting lamp 3, a reflector 8, a pair of resonant mirrors 5, 6 and a cooling arrangement 7, 9. The wavelength of a laser radiation is determined by the type of a laser rod. The duration of the laser impulse and its energy are primarily set by the power source associated with the laser device. Among lasers most commonly used in the medical field are solid-state lasers utilizing crystals of yttrium aluminum garnet doped by ions of neodymium, erbium, holmium, and also ruby laser on the basis of emery doped by atoms of chromium.

The portability is an important aspect for the effective usage of the medical laser devices. In this respect, miniature laser devices capable of being fitted in a hand of an operator are of great interest to the medical professionals. Among major elements of such handheld laser devices are: a cooling arrangement and a system of aiming and focusing of a laser beam. A power source of such laser device can be positioned either inside or outside of the casing. In the hand-held laser devices a special attention has to be paid to minimizing their dimensions and weight. Exciting lamps, which are mainly used in pulsed solid-state lasers, emit optical radiation which is within the range between 0.2 and 0.7 microns. This range is substantially greater than an absorption band of the laser rod. Therefore, a considerable portion of the exciting lamp optical radiation which passes through the laser rod is wasted by converting into a useless thermal energy. As a result, when the exciting lamp constantly pulses its radiation in the direction of the laser rod to generate a required laser output beam, the temperature of the laser rod rises, diminishing its efficiency. For example, when the temperature of the erbium laser rod rises to 70° C., the laser radiation is almost absent. This makes an efficient cooling arrangement to be a very important component of stable and efficient operation of solid-state laser rod assemblies. In resolving these problems an important factor is that an extensive pulsed thermal energy must be dissipated from a very small surface of the laser rod. Thus, development of effective, miniature cooling arrangements adapted for the removal of thermal energy from the laser rod assemblies is considered to be a key problem in the development of hand-held laser devices.

Currently, there are two basic methods utilized to facilitate heat dissipation from the laser rod assemblies. The first method is based on utilization of a gaseous cooling medium, whereas according to the second method, the liquid cooling medium is used. Minimal absorption of the exciting lamp optical radiation by the coolant, stability of the optical medium and relatively small weight and size of the cooling system are among important advantages of the first method. The liquid cooling of the second method provides considerably higher (compared to the gaseous cooling) heat transfer efficiency from the laser rod to the coolant. On the other hand, use of the liquid coolants does not provide the long-term stability of the optical medium, and often leads to contamination of the optical surfaces of the laser rod, exciting lamp and reflector. Furthermore, the currently available liquid cooling arrangements substantially increase weight and dimensions of the respective laser devices.

It is known that the amount of heat which has to be removed from a laser rod or crystal is dependent upon the following factors: the size of the cooling surface; the difference between the temperature of the laser rod and the temperature of the cooling agent, as well as the speed of the cooling agent in the vicinity of the laser rod surface. When the liquid cooling is utilized, the coefficient of heat transfer is much greater than that of the gas cooling. This is the reason why in the pulsed laser devices, the gas cooling is used very infrequently. However, utilization of the liquid cooling for the cooling of the laser rods and the exciting lamps increases the dimensions of the laser emitter, as well as brings up many other problems associated with the liquid cooling discussed hereinabove.

There are also known cooling arrangements for laser devices which combine the usage of the gaseous and liquid cooling principles. One such arrangement is disclosed by U.S. Pat. No. 5,481,556. According to this disclosure the outer casing of laser cavity containing an exciting lamp, a laser rod and a reflector is cooled by a liquid circulating within a closed circuit surrounding the laser cavity. The liquid coolant and the laser cavity are cooled by an air flow generated by a fan situated within the housing. One of the major drawbacks of this arrangement is that the heat removal from the laser rod is carried out indirectly through cooling of the exterior of the entire laser cavity. This approach substantially diminishes the efficiency of the laser assembly cooling process.

SUMMARY OF THE INVENTION

One aspect of the invention provides a hand-held laser device containing a casing formed with a substantially hollow interior space. A laser emitter is provided within the interior space and includes at least an exciting lamp and a laser rod. A source generating a stream of gaseous coolant is provided within the interior space. A fluid cooling arrangement at least partially surrounding the laser rod is disposed within the stream of gaseous coolant for heat removal therefrom.

The fluid cooling arrangement can be in the form of a liquid cooling arrangement which comprises a housing having an elongated opening passing therethrough. The elongated opening is adapted to at least partially receive the laser rod. An intermediate accumulation chamber is disposed within the casing, so as to communicate with the housing.

As to another embodiment of the invention, at least one connecting element for communication between the housing and the intermediate accumulation chamber is provided. A pumping arrangement is associated with the connecting element, so as to provide circulation of a liquid coolant between the housing and the intermediate accumulation chamber. A buffer space is formed between the exterior and interior walls of the casing. The buffer space communicates with the intermediate accumulation chamber. The exterior of the housing and intermediate accumulation chamber are situated within the stream of gaseous coolant, so as to facilitate heat removal from the liquid coolant contained thereinside. A plurality of cooling fins are formed of a heat conducting material and extend from the inner wall of the casing. The plurality of cooling fins are positioned within the stream of gaseous coolant for heat removal from the liquid coolant situated within the buffer space.

As to a further embodiment of the invention, a hand-held laser device is provided consisting of an elongated casing formed with a substantially hollow interior space. A laser emitter is formed by at least an exciting lamp and a laser rod. A low pressure zone is generated within the interior space to facilitate formation of a stream of gaseous coolant thereinside. An inlet opening is situated at a front end of the housing. A low pressure zone is formed at the rear end of the housing. A stream of gaseous coolant enters the interior space through the opening and axially extends in the front to rear direction for heat removal from the laser emitter. A filter is provided at an inlet opening for filtering a stream of gaseous coolant entering the interior space. Alternately, an inlet opening can be formed at a rear area of the housing, so that upon entering the interior space, the stream of gaseous coolant initially moves axially in the rear to front direction and then moves in the front to rear direction.

A still another embodiment of the invention provides a cooling arrangement for a hand-held laser device which consists of a laser emitter formed by at least a laser rod and exciting lamp. A jacket is defined by spaced from each other exterior and interior walls. A longitudinal opening is developed within the jacket and adapted to rotatably receive the laser rod. A continuous internal spiral groove is provided within a body of the jacket adjacently to the interior wall thereof, so as to provide positive displacement of a cooling fluid within the internal groove about an outer periphery of the laser rod during rotation of the jacket about the laser rod.

A still further embodiment of the invention provides a cooling arrangement for a laser device which includes a laser emitter formed by an exciting lamp and a laser rod. A jacket having a longitudinal interior opening which is stationary positioned with respect to the laser rod. An external continuous spiral arrangement is provided at an outer periphery of the laser rod. Rotational motion of the continuous external spiral arrangement results in the rotary positive displacement of a cooling fluid along the laser rod.

As to still another embodiment of the invention, a hand-held laser device includes a laser emitter with a laser rod having a frustoconical configuration or being shaped as a frustum of polygonal pyramid. The laser rod can also be formed having a substantially conical configuration.

BRIEF DESCRIPTION OF THE DRAWINGS

Other advantages and features of the invention are described with reference to exemplary embodiments, which are intended to explain and not to limit the invention, and are illustrated in the drawings in which:

FIG. 1 is a schematic diagram of a laser emitter according to the prior art;

FIG. 2 is a partial cross-sectional view of an embodiment of the invention utilizing gaseous and liquid cooling agents;

FIG. 6 is a partial cross-sectional view showing an interior of a hand-held laser device according to a still further embodiment of the invention;

FIG. 7 illustrates an alternative design of the laser rod assembly;

DESCRIPTION OF THE PREFERRED EMBODIMENT

Figure 3:
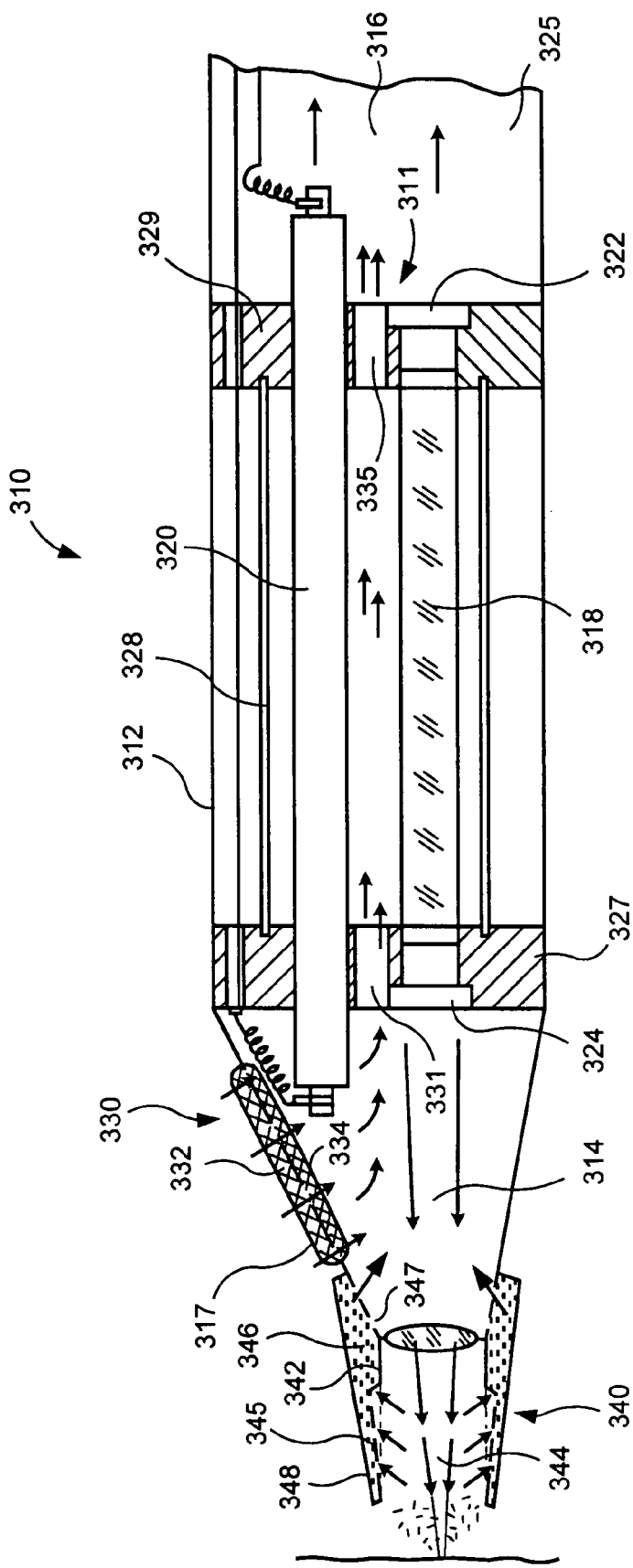
FIG. 3 is a partial cross-sectional view showing an interior of a hand-held laser device according to another embodiment of the invention.

Referring now to FIG. 2, illustrating one embodiment of a portable, hand-held laser device 10 having a laser emitter 11 disposed in a substantially hollow, elongated casing 12 which extends longitudinally between front 14 and rear 16 ends thereof. The casing is formed by exterior 15 and interior 17 walls defining a buffer space 48 therebetween. We shall revert to this structure later on in the application. Within an interior of the casing a laser rod 18 is disposed substantially centrally with an exciting lamp 20 being spaced therefrom. A fully-reflective or rear resonant mirror 22 is positioned at a rear end of the laser rod and at an optical axis thereof. An output or front resonant mirror 24 is situated in front of the laser rod at an optical axis thereof. A laser beam forming arrangement or focusing lens 26 is housed at the front end 14, so that the output mirror 24 is interposed between the laser rod 18 and the lens 26. To facilitate passage of the laser beam the output resonant mirror 24 is formed with reduced reflective characteristics relative to the fully reflective rear resonant mirror 22. Alternatively, the mirror 24 can be formed with an opening in the central area thereof. The laser rod 18 and the exciting lamp 20 are at least partially surrounded by a reflector 28.

During operation of the portable laser device, the flash lights are emitted from the exciting lamp 20 which is powered by a drive power source (not shown). The flash lights are reflected on the inner surface of the reflector to cause the laser rod to absorb the generated energy. A light is injected from the exciting lamp 20 into the laser material of the laser rod 18 initiating the discharge of photons in the crystal. These photons travel between the front 24 and rear 22 resonant mirrors producing a harmonic amplification. A laser light emitted from the laser rod is resonated and amplified by resonating mirrors. The amplified laser beam escapes the system through the output mirror 24. The emitted laser light beam is focused by the lens 26 and is incident upon either an optical fiber to be transmitted to a laser probe positioned at the front end of the apparatus or directly targeted on a body of a patient.

A cooling system of the laser device 10 illustrated in FIG. 2 is of a combined liquid-gaseous type. A convective cooling arrangement or cooling fan 30 generating a stream of gaseous coolant, such as an ambient air, for example, is provided within the interior of the casing 12 at the rear end 16. The liquid cooling arrangement includes a housing 32 formed by spaced from each other interior and exterior walls thereof 34 and 36, respectively. A cooling chamber 38 adapted to receive a liquid cooling medium is formed within the hollow space between the walls of the housing 32. The interior wall 34 defines an elongated opening 40 extending through the entire length of the housing and adapted to at least partially receive the laser rod 18. The walls 34 and 36 of the housing are made of an optically transparent material. An intermediate accumulation chamber 42 is provided within the casing 12 and is connected to the cooling chamber 38 by means of inlet and outlet connecting elements 44 and 46, respectively. In order to increase the volume of the available liquid cooling medium and to further intensify the cooling process, the buffer space 48 is provided within the interior space of the casing 12 along the exterior wall thereof 15. Communication between the buffer space 48 and the intermediate accumulation chamber 42 is accomplished by means of input 52 and discharge 54 elements. A multiplicity of fins 56 extends outwardly from the inner wall 17 of the casing toward a central region of the apparatus 10.

In the cooling system of the hand-held laser device 10 each of the gaseous and liquid cooling agents are applied to different elements of the laser unit 11. In this respect, the stream of a gaseous cooling agent, such as air, for example, generated by the fan 30 and directed longitudinally within the casing is typically directed toward the elements of the laser unit exposed to the maximal temperature. Most specifically, it is directed toward the exciting lamp 20 and the reflector 28. On the other hand, the laser rod 18 is cooled by the liquid cooling medium, such as water, for example, circulating primarily between the cooling chamber 38, the intermediate accumulation chamber 42 and the buffer space 48. In the embodiment of FIG. 2 the liquid coolant is supplied to the cooling chamber 38 from the intermediate accumulation chamber 42 by means of a pump 43 associated with the inlet connecting element 44. Upon circulation within the cooling chamber 38, the liquid coolant having an elevated temperature is recycled to the intermediate accumulation chamber 42 through the outlet element 46 and ultimately can re-enter the buffer space 48 through the discharge element 54. An auxiliary cooling element 58 having a thermal contact with the wall of the intermediate accumulation chamber 42 can be provided for intensifying the cooling process.

As illustrated in FIG. 2, the flow of gaseous coolant generated by the fan 30 is directed to the exterior surfaces of the elements forming the liquid cooling system such as: the cooling chamber 38 and the intermediate accumulation chamber 42. The multiplicity of fins 56 increases the heat exchanging surface of the interior wall 17 forming the buffer space 48 which is also subject to the flow of gaseous coolant. To further intensify the flow of gaseous coolant within the casing 12, the rear 16 and front 14 regions thereof are provided with openings 58, 60, respectively.

The elements of the hand-held laser device 10 subjected to the maximum temperature, such as the exciting lamp 20 and the reflector 28 are effectively cooled by the steam of gaseous coolant generated by the fan 30. On the other hand, the temperature of the laser rod 18 is reduced directly by the flow of liquid coolant. Furthermore, the elements of the liquid cooling system are also cooled by the stream of gaseous coolant generated by the fan 30. Such combined cooling capability provides the required stability of the temperature of the laser rod 10 which generate under the conditions of hand-held laser device.

The effectiveness of heat removal from the laser rod unit 11 can be enhanced by increasing the velocity, speed and rate of flow of the gaseous coolant along its elements. In the embodiment of FIG. 2, this can be accomplished through the increase in the rotational speed of the fan 30 or through a provision of an outside air pump supplying a relatively high pressure gaseous coolant inside the casing of laser device. In the laser device illustrated in FIG. 2 the gaseous cooling arrangement is adapted to utilize the ambient air as the gaseous cooling medium and water as a liquid cooling medium. However, utilization of other gaseous and liquid cooling agents which can be pre-cooled prior to entering the interior of the casing is also contemplated. One of the examples of such pre-cooled gaseous agent can be carbon dioxide.

Referring now to FIG. 3, illustrating another embodiment of the invention. The hand-held laser apparatus 310 is formed with an elongated casing 312 having a substantially hollow internal area extending between front 314 and rear 316 ends thereof. The emitter assembly 311 including the laser rod 318, the front 324 and rear 322 resonant mirrors, the exciting lamp 320 and the reflector 328 are supported by spaced from each other support elements 327 and 329. A low pressure or vacuum zone 325 is provided at the rear end 316. In the embodiment of FIG. 3 a stream of gaseous coolant enters the interior of the casing through an inlet opening 317 disposed at the front end 314 and is discharged through an exit opening provided at the rear end of the device (not shown). The low pressure zone 325 results in the pressure differential between the rear and front ends, so that a longitudinal flow of gaseous coolant is generated passing along the laser rod 318, the exciting lamp 320 and other elements of the emitter assembly. To facilitate passage of the coolant the support elements 327 and 329 are formed with apertures 331 and 335, respectively. The low pressure zone can be generated at the front 314 or rear 316 of the casing by any conventional means such as an air pump, etc. which can be positioned inside or outside of the casing 312. Such arrangement results in the high speed of the gaseous coolant flow and assures smaller dimensions of the cooling system. Furthermore, in comparison with a fan which has been typically utilized to provide a flow of gaseous coolant, the low pressure zone requires less power to be energized. Another important advantage of the low pressure zone 325 is that it substantially improves homogenuity of the gaseous coolant flow within the interior of the casing and substantially eliminates gaseous vortexes and stagnation areas thereinside.

The gaseous coolant entering the interior of the casing typically contains particles of an environmental dust as well as particles of substances treated by a laser device. Such particles, when passing through the interior of the casing contaminate optical elements disposed thereinside. This ultimately results in diminishing the essential characteristics of the laser device. To minimize this undesirable effect, a filtration unit 330 containing an exterior, disposable filter 332 and an interior, long lasting filter 334 is provided at the inlet 317.

In medical applications of the hand-held laser apparatus 310 the gaseous coolant may also contain particles of human flesh (debris) formed during interaction of the laser beam with a treated tissue. Such debris are considered to be a possible pathogen and need to be evacuated from the air for further proper disposal. To serve this purpose a disposablde filter 340 can be provided at the front end of the apparatus 310. As illustrated in FIG. 3, the filter 340 includes an inner wall 342 defining a central aperture 344 passing through the entire length thereof. A substantially hollow space 346 formed between the interior wall 342 and exterior wall 348 is adapted to receive a filtering material therein. A multiplicity of inlet openings 345 are disposed at the front region of the inner wall 342, whereas the outlet apertures 347 are provided at the rear region of the filter. In view of the lower pressure zone 325 and the suction process associated therewith, the air stream containing particles of human flesh initially enter the interior of the filter 340 through the multiplicity of openings 345. Upon passage through the filtering material, the air stream separated from the particles and debris enters the front region 314 of the apparatus through the outlet openings 347.

Figure 4:
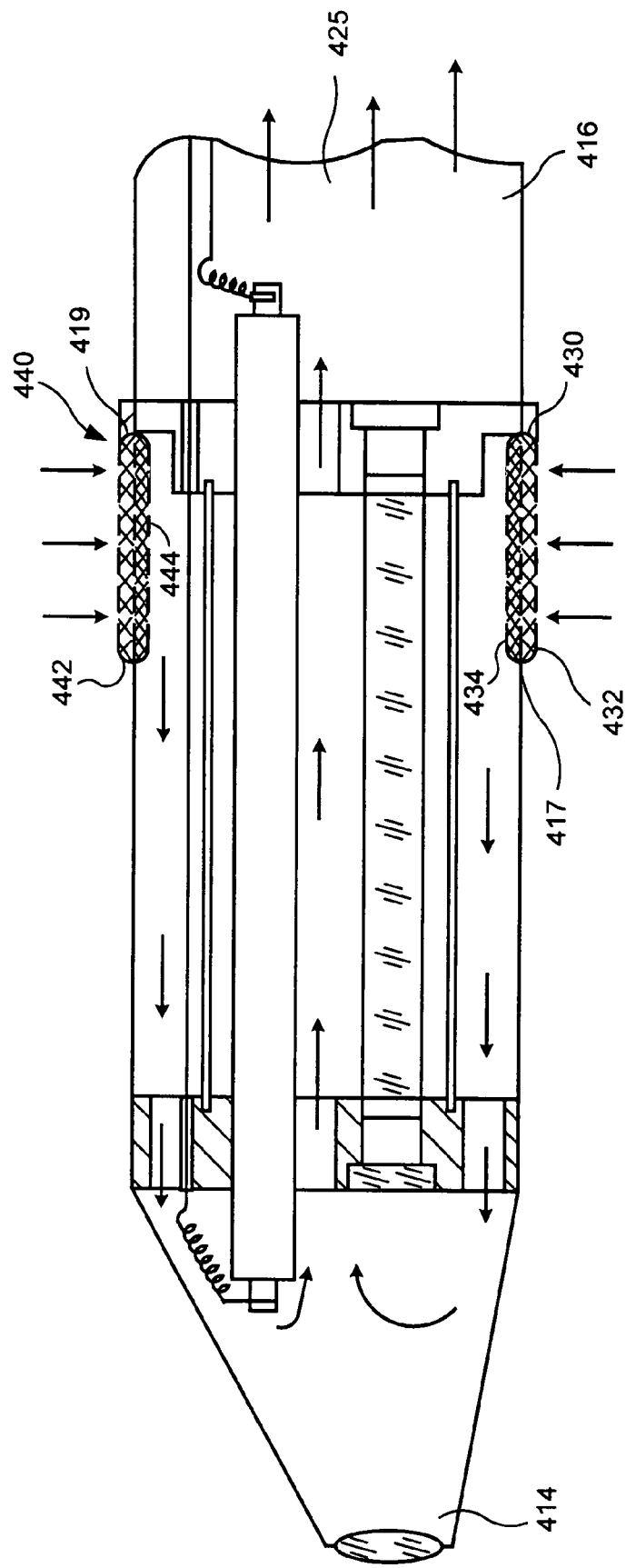
FIG. 4 is a partial cross-sectional view showing an interior of a hand-held laser device according to a further embodiment of the invention.

The embodiment of FIG. 4 is in many respects similar to the embodiment of FIG. 3. However, the inlet openings 417 and 419 containing the respective filtering units 430 and 440 are positioned at the rear region 416 of the laser emitter. As illustrated in FIG. 4, the flow of gaseous coolant upon entering the interior of the casing through the respective exterior and interior filters 432, 434 and 442, 444 is initially directed toward the front region 414 of the device enhancing heat dissipation from the exterior of the laser emitter. At the front region 414 the flow of gaseous coolant is diverted back toward the low pressure zone 425, so as to circulate along the interior area of the laser emitter. In the embodiment of FIG. 4 the stream of gaseous coolant enters the interior of the casing at the rear end thereof where concentration of particles resulted from the usage of the device is lower than at the front of the device.

It should be noted that the low pressure or vacuum zone can be also used in the embodiment of FIG. 2 instead of the fan to generate a flow of gaseous coolant within the housing. In the embodiment of FIG. 2 the low pressure zone can be provided, for example, at the front region of the housing.

Figure 5:
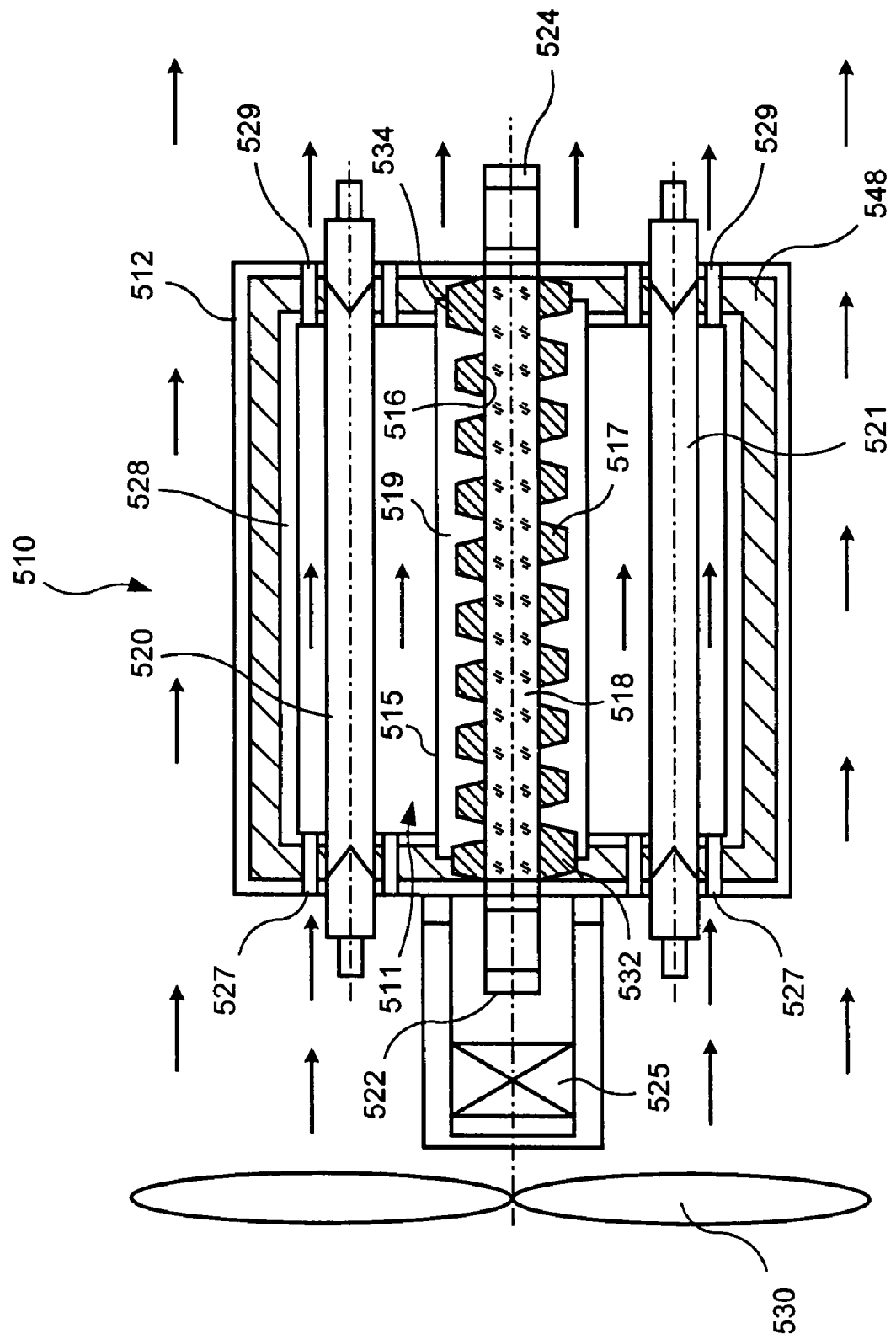
FIG. 5 is a partial cross-sectional view showing an interior of a hand-held laser device according to still another embodiment of the invention.

Turning now to FIG. 5, which illustrates another embodiment of a cooling arrangement 510 for a hand-held laser device. A laser emitter 511 consists of two exciting lamps 520 and 521 which are disposed on opposite sides of the laser rod 518. In the longitudinal direction the laser rod 518 is interposed between the fully reflective rear resonant mirror 522 and a semi-reflective output or front resonant mirror 524. The lamps and the laser rod are surrounded by a reflector 528 which is positioned within and spaced from the outer casing 512. A substantially hollow buffer space 548 is formed between the outer casing 512 and the reflector 528.

A jacket 519 made of an optically transparent material is disposed along an exterior surface of the laser rod 518. The jacket is defined by at least an exterior surface 515 and a longitudinal interior opening 516 passing therethrough. A continuous internal spiral groove 517 is formed within a body of the jacket at the opening 516 and extends through the entire length thereof. The longitudinal opening including the internal groove is adapted to rotationally receive the exterior surface of the laser rod 518. The rotational motion of the jacket 519 relative to the laser rod is facilitated by a small gap provided between the internal opening 516 of the jacket and the outside surface of the laser rod. The internal spiral groove 517 is adapted to receive the cooling liquid and pass it along the exterior surface 515 of the laser rod. To increase the volume of the available liquid cooling and to further intensify the cooling process, the internal spiral groove 517 is in fluid communication with the buffer space 548 also filled with the liquid coolant. A conventional rotational arrangement, such as an electric motor 525 provided with a magnetic clutch, for example, generate rotational motion of the jacket 519 including the internal spiral groove 517 relative to the laser rod 518.

In the embodiment of FIG. 5 the cooling fan 530 is positioned rearwardly from the casing 512. To facilitate entering and exiting the flow of gaseous coolant generated by the fan 530 into and from the laser cavity, apertures 527 and 529 are formed within rear and front walls of the casing, respectively. In operation the inner space of the continuous spiral groove 517 and the buffer space 548 are filled with the liquid cooling medium. The rotational motion of the jacket 519 including the continuous internal spiral groove 517 relative to the stationary laser rod 518 provides longitudinal motion of the liquid coolant medium along the exterior surface 515 of the heated laser rod. The continuous spiral groove communicates with the buffer space 548 filled with the liquid coolant. To further enhance the efficiency of the laser rod cooling, the cooling fluid circulates between the buffer space and the internal spiral groove. After being discharged from the groove 517, the spent cooling liquid having an elevated temperature upon entering the buffer space 548 transfers its heat to the casing 512 which is absorbed by the air stream generated by the fan 530.

In the embodiment of FIG. 5, the close rotational fit between the continuous spiral groove 517 of the jacket and the exterior surface 515 of the laser rod form a plurality of enclosed cavities which move continuously from the inlet 532 to outlet 534 of the laser rod assembly. This arrangement results in the positive pressure capability for the liquid coolant. In use these cavities trap the liquid coolant agent at the inlet 532 carry it along the outer surface 515 of the laser rod and discharge at the outlet 534, providing uninterrupted flow of the coolant along the laser rod. Thus, the rotational motion of the internal spiral groove 517 along the laser rod form a positive-displacement arrangement, which is capable of moving a definite quantity of the liquid coolant with every revolution of the spiral groove.

Turning now to FIG. 6, illustrating another embodiment of the invention. A laser rod assembly consisting of a laser rod 618, the fully reflective rear resonant mirror 622 and the output, semi-reflective front resonant mirror 624 are movably associated with a shaft of the electrical motor 625 or any other conventional rotational arrangement. An outwardly extending continuous spiral arrangement 627 is wound around or distributed over the outer surface 615 of the laser rod 618. The spiral arrangement 627 can be carved out from a body of the laser rod. Alternatively, an independent spiral arrangement can be positioned over the exterior surface of the laser rod. In this manner a continuous external spiral groove formation 629 is developed over the outer surface 615 of the laser rod. A jacket 619 defined by at least the internal longitudinal opening 628 and external surface 619 is formed of an optically transparent material. The exterior surface 619 of the jacket is fixedly positioned within the interior of the casing (not shown), whereas the internal longitudinal opening 628 is adapted to rotationally receive the laser rod 618 with the continuous external spiral arrangement 627. This rotational motion is facilitated by a minor gap provided between the outer extremities of the spiral arrangement and the interior surface of the jacket 619. As in the previously described embodiments the exciting lamp 620 is provided in spaced relationship from the laser rod.

In the embodiment of FIG. 6, the rotation motion of the laser rod 618 within the longitudinal opening 628 provides rotary positive displacement in which the flow of liquid coolant is axially directed through the opening, for heat removal from the outer surface 615 of the laser rod. The coolant is carried by the outwardly extending threads on the rotational laser rod and is displaced axially as the spiral rotates.

In operation, upon activation of the rotational arrangement by the electrical motor 625, the laser rod along with the continuous spiral arrangement and resonant mirrors 622 and 624 are rotated within the inner hollow space of the optically transparent jacket. The rotational motion of the external spiral develops suction at the inlet of the jacket 619, so that the coolant is introduced into the gap between the laser rod and the interior of the jacket. Upon passing through hollow space of the jacket, the heat exchanging process is taking place between the coolant and the external surface of the laser rod lowering its temperature. When the frequency of rotation of the laser rod exceeds the pulse frequency of the exciting lamp, one flash pulse of the exciting lamp corresponds to the several revolutions of the laser rod. This condition results in the increased uniformity of the laser beam generated by the device of the invention.

In the embodiment of FIG. 6 the temperature of the laser rod is reduced by the flow of the coolant developed during the rotation of the laser rod and the external spiral arrangement about the longitudinal axis of the device. In this case the speed of the flow of the coolant at the surface of the laser rod in addition to the axial component also has a radial component which directly dependent upon a rotational speed of the laser rod. Thus, the quantity of heat removed from the rod is dependent upon the rotational speed thereof. If the rotational speed of the rod exceeds the repetition rate of the laser pulses, then the uniformity of the laser beam over its cross section will increase respectively. It has been determined that upon the increase of the ratio of the rotational speed of the laser rod to the repetition rate of the laser pulses, the higher uniformity of the laser beam will take place.

In an alternative embodiment the spiral arrangement 27 can be rotated within the internal longitudinal opening 628 of the jacket about a stationary positioned laser rod.

It should be noted that the coolant displacement arrangement as discussed hereinabove with reference to FIG. 6 can be utilized in the hand-held laser apparatus of FIG. 2. In this respect, the laser rod formed with the continuous external spiral arrangement is rotationally positioned within the internal space of the cooling chamber which communicates with the intermediate accumulation chamber by means of the inlet and outlet connecting elements. Upon rotation of the laser rod including the external spiral arrangement suction is developed at the inlet connecting element, so as to bring the liquid coolant from the intermediate accumulation chamber into the interior space of the cooling jacket. The spent liquid coolant having elevated temperature is discharged back to the intermediate accumulation chamber through the outlet connecting element. The rotational motion of the laser rod and the external spiral arrangement generates suction within the cooling chamber ultimately resulted in an uninterrupted flow of the coolant along the rod. In view of that, the special pumping arrangement utilized in the embodiment of FIG. 2 for bringing the liquid coolant from the intermediate accumulation chamber into the cooling chamber is no longer required.

In the embodiment of FIG. 7 the laser rod 718 is formed having a frustoconical configuration or a shape of a frustum of polygonal pyramid. A lateral or side surface 726 of the rod extends between first 732 and second 734 bases which are substantially normal to the optical axis A-A of the device. The exciting lamps 720 and 721 are disposed on both sides of the laser rod 718. The bases 732 and 734 as well as the lateral surface 726 of the laser rod are transparent to the radiation of the exciting lamps. Similar to the previously described embodiments, the laser rod 718 is interposed between the fully reflective rear resonant mirror 722 and a semi-reflective front resonant mirror 724. The front resonant mirror 724 faces the first base 732 of the laser rod having a cross section substantially smaller than the second base 734 which faces the fully reflective rear resonant mirror 722. As illustrated in FIG. 7, the flow of the cooling medium extends along the longitudinal axis A-A of the laser rod 718 in the front to rear direction. The lateral surface 726 of the laser rod is subject to a stream of coolant extending along the longitudinal axis A-A of the laser rod.

As illustrated in the diagram forming a part of FIG. 7 at the area of engagement with the lateral surface 726 the directional vector of the velocity V of the stream of coolant can be broken into a component $V_n$ which extends substantially normally to the lateral surface and a tangential component $V_t$ directed along the lateral surface. It is known that the normally directed stream of coolant provides the cooling process of greater efficiency compared to the arrangement in which the entire stream of coolant is directed only tangentially or along the surface of the laser rod.

In the embodiment of FIG. 7 the existence of the normal component $V_n$ in the velocity of the flow of coolant reduces stagnation areas of the coolant flow caused by the frictional forces between the surface of the laser rod and the flow of coolant. This arrangement further increases the efficiency of the heat transfer between the laser rod to the coolant.

In the laser apparatus of FIG. 7 an outside periphery or diameter of the fully reflective rear resonant mirror 722 exceeds the largest cross section of the laser rod 718. In this respect, it is illustrated in FIG. 7 that the outside periphery of the rear mirror 722 is greater than the outside periphery of the rear base 734. Thus, upon multiple reflections of the optical radiation between the fully reflective rear resonant mirror 722 and lateral surface 726 of the laser rod, an additional amplification of the laser radiation has taken place. This is most common when the angle at the tip of the laser rod 718 is about 90°.

Figure 8:
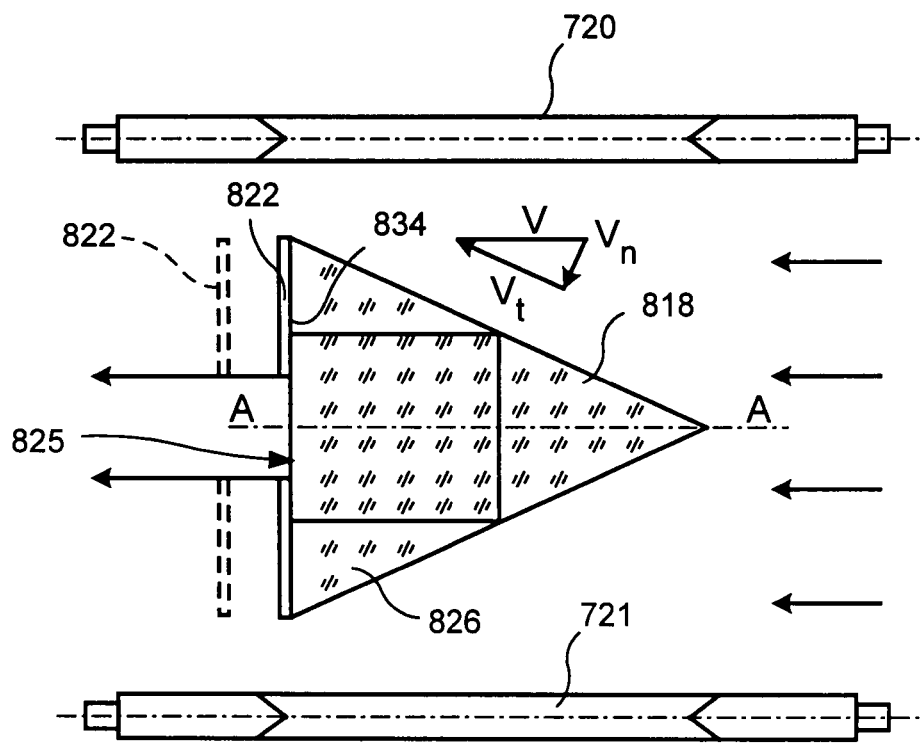
FIG. 8 shows the assembly having a conically-shaped laser rod.

Turning now to FIG. 8 which illustrates a further embodiment of the invention with a laser rod 818 having a substantially conical configuration or formed in the shape of polygonal pyramid having one base 834. The lateral surface 826 and the base 834 of the laser rod are transparent to the optical radiation. The fully reflective resonant mirror 822 is provided with a central opening 825 for discharging the laser beam radiation generated by the device. The resonant mirror 822 can be attached to the base 834 or can be spaced from the base 834 (as shown in phantom). The resonant mirror 822 can be formed by applying a special reflective coating to the base 834. The laser rod 818 is interposed between two exciting lamps 720 and 721.

As illustrated in FIG. 8, the flow of cooling medium is directed along the longitudinal axis A-A of the laser rod 818. Similar to the embodiment of FIG. 7, at the area of engagement of the flow of coolant with the lateral surface 826 the directional vector V of the velocity of the coolant stream is formed with a normal component $V_n$ extending substantially normally to the lateral surface 826 and a tangential component $V_t$ directed along the lateral surface 826. In a manner similar to the above-discussed, the normally directed stream provides the cooling process of greater efficiency compared to the arrangement in which the entire stream of coolant is directed only tangentially or along the surface of the laser rod. This arrangement also increases the efficiency of the heat transfer between the laser rod 818 to the coolant medium.

Figure 9:
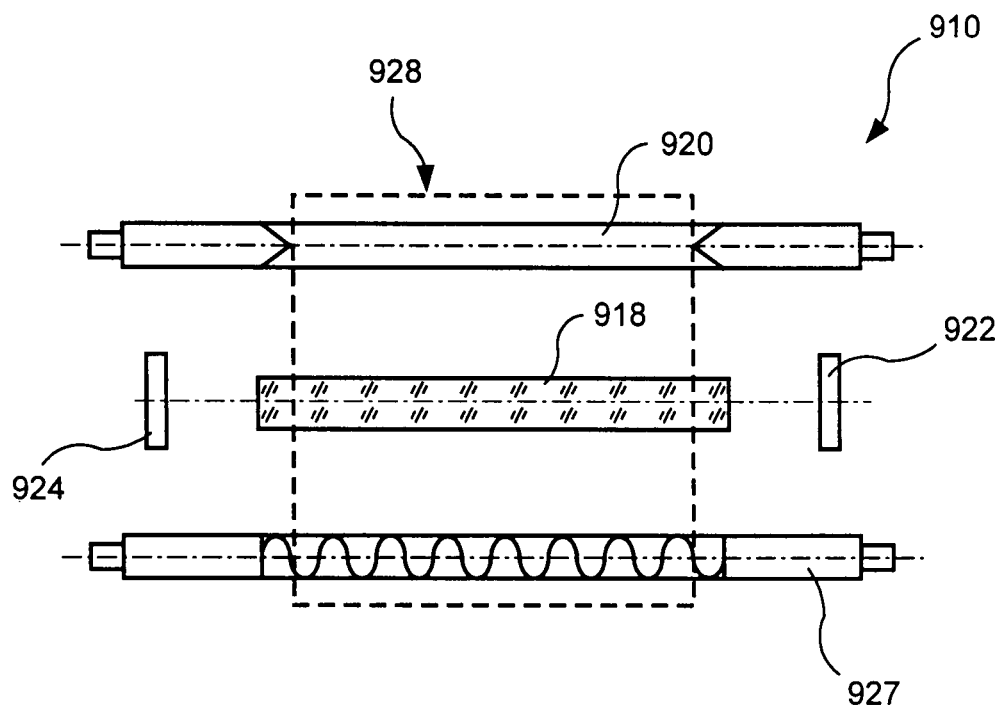
FIG. 9 illustrates an embodiment of the invention with a pulsed laser emitter utilizing an additional lamp providing a continuous visible optical irradiation.

Turning now to FIG. 9 illustrating the pulsed laser device 910 having the laser rod 928, front and rear resonant mirrors 924 and 922 and the exciting lamp 920 situated within the reflector 928. A source of continuous optical radiation 927 is provided within the reflector on a side of the laser rod 918 opposite to the exciting lamp 920. The source 927 should be positioned in such a way as to minimally interfere with interaction between the laser rod and the exciting lamp. A part of a continuous visible optical radiation generated by the source 927 and amplified in the rod 928 serves as a pilot visual light to enhance targeting of an infrared laser beam at a treated area. Furthermore, the continuous optical radiation after being absorbed by the laser rod reduces a lazing-action threshold. This enables the invention to reduce the electrical power consumed by the exciting lamp 920 so as to ultimately reduce the temperature of the laser rod 918.

What is claimed is:

1. A cooling arrangement for a hand-held laser device, comprising:
   a laser emitter formed by at least a laser rod and an exciting lamp spaced from each other;
   a jacket defined by at least spaced from each other exterior and interior walls thereof, a longitudinal opening extending through said jacket and defined by said interior wall, said longitudinal opening being adapted to rotatably receive said laser rod; and a continuous internal spiral groove formed within a body of said jacket at said interior wall, so as to provide positive displacement of a cooling fluid within said internal groove about an outer periphery of said laser rod during rotation of said jacket about said laser rod.

2. The cooling arrangement according to claim 1, wherein said cooling fluid is a cooling liquid, said laser emitter further comprises a reflector at least partially surrounding said laser rod and said exciting lamp; a housing is separated from said reflector by a substantially hollow area, so as to form a buffer space therebetween.

3. The cooling arrangement according to claim 2, wherein said buffer space is connected to said internal spiral groove, to provide fluidal communication therebetween.

4. The cooling arrangement according to claim 2, further comprising a source for generating a stream of gaseous coolant situated externally of said casing.

5. The cooling arrangement according to claim 4, wherein said source is a rotating fan and said casing is formed with a plurality of apertures facilitating entering and exiting said flow of gaseous coolant with respect to the interior of the housing.

6. The cooling arrangement according to claim 5, wherein said casing is positioned within the stream of gaseous coolant, so as to facilitate heat removal from the liquid coolant situated within the buffer space.

7. A cooling arrangement for a laser device comprising:
a laser emitter formed by at least an exciting lamp and a laser rod spaced from each other;
a jacket stationarily positioned with respect to said laser rod unit, said jacket having a longitudinal interior opening extending therethrough to receive the laser rod; and
a continuous spiral arrangement is provided in the body of the jacket at an outer periphery of the laser rod and extending outwardly therefrom,
whereby rotational motion of the continuous external spiral arrangement provides a rotary positive displacement of a cooling fluid along said laser rod.

8. The cooling arrangement according to claim 7, wherein said continuous external spiral arrangement is fixedly associated with the outer periphery of the laser rod, said cooling fluid is a cooling liquid which is carried out by said continuous external spiral arrangement, so as to be axially displaced upon rotation of the laser rod.

9. A cooling arrangement according to claim 8, wherein said continuous external spiral arrangement is carved out from the body of said laser rod.

10. The hand-held laser device according to claim 7, wherein said continuous external spiral arrangement is rotatable independently of said laser rod.

* * * * *